(12) United States Patent
Su et al.

(10) Patent No.: US 7,074,963 B2
(45) Date of Patent: Jul. 11, 2006

(54) PREPARATION OF SECONDARY AMINES

(75) Inventors: Wei-Yang Su, Austin, TX (US);
Christopher H. Nelli, Austin, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 171 days.

(21) Appl. No.: 10/623,293

(22) Filed: Jul. 18, 2003

(65) Prior Publication Data

US 2004/0019238 A1    Jan. 29, 2004

Related U.S. Application Data

(63) Continuation-in-part of application No. 10/200,361, filed on Jul. 22, 2002, now abandoned.

(51) Int. Cl.
*C07C 209/26* (2006.01)

(52) U.S. Cl. .................. 564/473; 564/398; 564/472

(58) Field of Classification Search .................. 564/1, 564/297, 298, 305, 310, 311, 313
See application file for complete search history.

(56) References Cited

U.S. PATENT DOCUMENTS

| | | | |
|---|---|---|---|
| 3,151,112 A | 9/1964 | Moss | 260/247 |
| 3,364,239 A | 1/1968 | Speranza | 260/347.7 |
| 3,522,309 A | 7/1970 | Kirby | 260/577 |
| 3,654,370 A | 4/1972 | Yeakey | 260/584 |
| 3,994,975 A * | 11/1976 | Oude Alink et al. | 260/563 |
| 4,040,799 A | 8/1977 | Oude Alink et al. | 44/75 |
| 4,330,677 A | 5/1982 | Linke et al. | 562/583 |
| 4,373,107 A * | 2/1983 | Tahara et al. | 564/473 |
| 4,521,624 A | 6/1985 | Jackisch | 564/446 |
| 4,904,751 A | 2/1990 | Speranza et al. | 528/45 |
| 4,927,912 A | 5/1990 | Speranza et al. | 528/405 |
| 4,946,924 A | 8/1990 | Speranza et al. | 528/111 |
| 4,952,734 A | 8/1990 | Weber et al. | 564/471 |
| 5,001,267 A * | 3/1991 | Speranza et al. | 564/472 |
| 5,093,528 A | 3/1992 | Dobson et al. | 564/472 |
| 5,225,597 A | 7/1993 | Kurek | 564/446 |
| 6,476,597 B1 | 11/2002 | Spratt et al. | 564/385 |

FOREIGN PATENT DOCUMENTS

AU    B-39042/89    1/1992

OTHER PUBLICATIONS

Database CAPLUS on STN, Acc. No. 1995:804792, Matsuo et al., JP 07173111 (abstract).
"Preparation of N-Alkyl-Substituted Poly(oxyalkylene) amines and their reactivities toward blocked isocyanates" Ind. Eng. Chem. Res 1997, 36, 4231-4235.

* cited by examiner

*Primary Examiner*—Brian Davis
(74) *Attorney, Agent, or Firm*—Ron D. Brown; Edward Korompai

(57) ABSTRACT

Disclosed herein is a process for the reductive alkylation of primary amines to form secondary amines, by high pressure reaction of the primary amine with an alkylating agent and hydrogen in the presence of a catalyst which comprises metallic palladium. A process of the present invention is characterized in having high conversion rates and high selectivities, both greater than 95% on a first pass through the reactor. According to a preferred embodiment, the secondary amine produced comprises at least one 2-alkyl group bonded to the nitrogen atom of the primary amine product.

18 Claims, No Drawings

PREPARATION OF SECONDARY AMINES

CROSS-REFERENCES TO RELATED APPLICATIONS

This Application is a Continuation-In-Part of and claims priority to, U.S. patent application Ser. No. 10/200,361 filed Jul. 22, 2002, now abandoned.

FIELD OF THE INVENTION

The present invention relates generally to catalytic processes for alkylations of amines, and in more particular to selective formation of secondary amines from primary amines. A process according to one embodiment of the invention is especially well-suited for preparing 2-alkyl substituted amines from primary amines.

BACKGROUND INFORMATION

Processes for producing organic amines have been known in the art for quite some time. For example, U.S. Pat. No. 3,994,975 relates to the reductive amination of unsaturated cyclic ketones; to cyclic amines prepared thereby; and to uses thereof. For example, when isophorone is reductively aminated, trimethyl cyclohexylamines and cyclohexenamines are obtained. The invention includes uses of the amine products as fuel additives for stabilizing distillate fuels.

U.S. Pat. No. 4,521,624 provides a process for the reductive amination of a saturated cyclic ketone which comprises reacting a saturated ketone with an amine in the presence of hydrogen and a hydrogenation catalyst, whereby said saturated cyclic ketone is converted to the corresponding cyclic amine.

U.S. Pat. No. 5,001,267 relates to secondary alkyl amine derivatives of ethylenediamine which are formed in a one-step reaction when ethylenediamine is substantially simultaneously continuously mixed with a methyl alkyl ketone to form a reaction mixture which is continuously hydrogenated in the presence of a hydrogenation catalyst and hydrogen. The alkyl group contains 1 to 4 carbon atoms.

U.S. Pat. No. 5,093,528 teaches a process for producing a secondary amine terminated polyether from a primary amine terminated polyether in which the primary amine terminated polyether is reacted at elevated temperature with a carbonyl compound in the presence of hydrogen and a catalyst composition comprising nickel, ruthenium and at least one other transition metal selected from the second or third row transition metals. The amount of carbonyl compound employed is in excess of the stoichiometric amount required to react completely with the ether. The secondary amine terminated polyethers are useful in the formation of polyurea elastomers.

While the prior art is replete with descriptions of processes for producing organic amines, there has been no work concerned with producing secondary amines selectively, for example, secondary amines derived from isophorone diamine using acetone in the presence of hydrogen and a catalyst to form secondary amines. When base metal catalysts (Ni, Co, etc.) are used, a high acetone to amine ratio is required and even under these conditions a low conversion to amine is observed. Also, amine dimer (amine coupling product) is formed in substantial amounts.

SUMMARY OF THE INVENTION

The present invention provides a process for producing secondary amines which comprises reacting a mixture comprising: a) hydrogen; b) a primary amine; and c) a carbonyl compound represented by the structure:

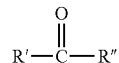

at any pressure in the range of 100.0 psig to 3000.0 psig, including every tenth psig therebetween, and at any temperature in the range of 80° C. to 230° C., including every degree therebetween, in the presence of an effective catalytic amount of a catalyst comprising metallic palladium having a surface area of at least 50 m² per gram, to yield a secondary amine product having formula:

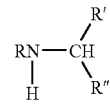

in which R is any alkyl, aminoalkyl, alkylaryl, or aminoalkylaryl group, whether straight-chain, branched, or cyclic, R' and R" are each independently selected from the group consisting of: hydrogen; $C_1$–$C_{20}$ alkyl, whether straight-chain, branched, or cyclic, subject to the proviso that both R' and R" are not simultaneously hydrogen, wherein the amount of tertiary amine produced during said process is less than 3.00% by weight of the total amount of secondary amine produced.

DETAILED DESCRIPTION OF THE INVENTION

The present invention is concerned with a process described by the general reaction:

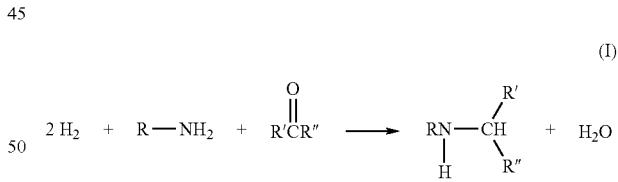

in which hydrogen, an amine and a carbonyl compound represented in the above reaction are reacted to alkylate the nitrogen atom of the primary amine raw material, wherein R may be any organic moiety including without limitation alkyl, aminoalkyl, alkylaryl, or aminoalkylaryl group, whether straight-chain, branched, or cyclic, including those which contain one or more oxyalkylene units such as ethoxy, propoxy and butoxy units; R' and R" may each independently be hydrogen or any $C_1$–$C_{20}$ alkyl group, straight-chain, branched, or cyclic, which is carried out in the presence of a catalyst comprising palladium on carbon, and which is carried out at any temperature in the range of between 80° C. to 200° C. and at any pressure in the range of between 100 psig to 3000 psig.

Reductive alkylations of amines which use catalysts and which are also carried out according to prior art methods typically yield a reaction product mixture which contains substantial amounts of tertiary amine products, coupling products, and unreacted starting materials. We now report our discovery that using a catalyst comprising palladium on carbon in the presence of hydrogen for the reductive alkylation of a primary amine with a ketone results in nearly complete selectivity of the primary amine to a 2-alkyl substituted secondary amine product, with only negligible amounts of impurities, in a single pass through a tubular reactor.

A process according to one preferred embodiment the invention is concerned with alkylation of isophorone diamine according to the reaction scheme:

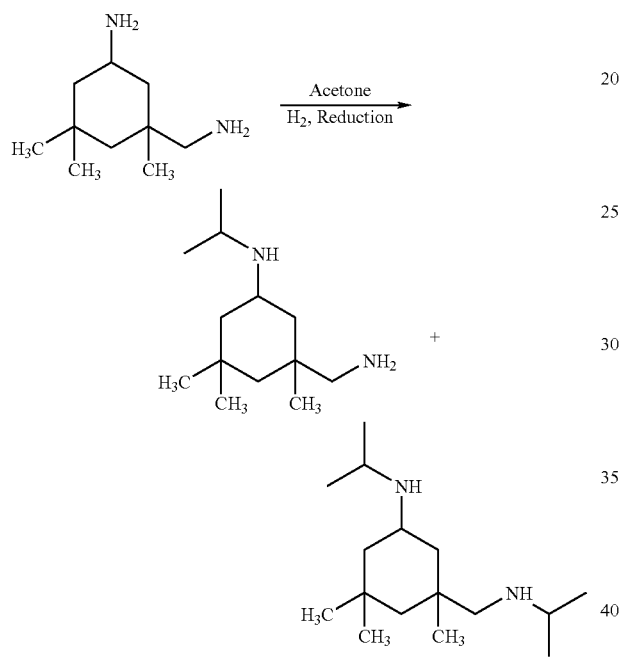

using a catalyst comprising palladium on carbon. In the above reaction, the starting material, isophorone diamine, is represented by the general formula R—NH$_2$ in the reaction in formula (I), wherein R is an aminoalkyl group.

However, in order to be suitable as a starting material for an alkylation process according to the present invention, the main requirement is that a material must have at least one —NH$_2$ group in its molecular structure. Thus, the present invention is useful in alkylating a wide variety of primary amines, including not only aliphatic and aromatic primary amines, but substituted and modified materials containing a primary amine function, including those mentioned above within the class known as polyoxyalkylene amines described by the formula:

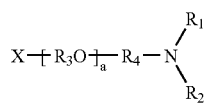

in which R$_1$ and R$_2$ are each independently selected from the group consisting of: hydrogen; an alkyl group having 1, 2, 3, 4, 5, or 6 carbon atoms, whether straight-chain or branched; or a radical of the formula:

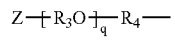

in which R$_3$ may be an alkyl group having any number of carbon atoms selected from 1, 2, 3, 4, 5, or 6, straight-chain or branched; R$_4$ is a straight-chain or branched alkyl bridging group having 1, 2, 3, 4, 5, or 6 carbon atoms; Z is a hydroxy group or alkyl group containing 1, 2, 3, 4, 5, or 6 carbon atoms, straight-chain or branched; q is any integer between 0 and 400; and wherein X is any of:

i) a hydroxy group or an alkyl group having any number of carbon atoms selected from 1, 2, 3, 4, 5, or 6; or ii) a group

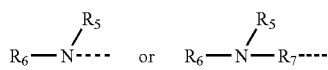

in which R$_5$ and R$_6$ are each independently selected from the group consisting of: hydrogen; an alkyl group having 1, 2, 3, 4, 5, or 6 carbon atoms, whether straight-chain or branched; or

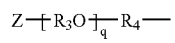

as defined above in which Z is a hydroxy group or an alkoxy group having 1, 2, 3, 4, 5, or 6 carbon atoms, and in which R$_7$ is a straight-chain or branched alkylene bridging group having 1, 2, 3, 4, 5, or 6 carbon atoms; or iii) a moiety of the formula:

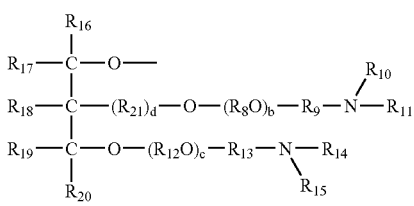

in which R$_{10}$, R$_{11}$, R$_{14}$, and R$_{15}$ are each independently selected from the group of: hydrogen; an alkyl group having 1, 2, 3, 4, 5, or 6 carbon atoms, straight-chain or branched; the moiety

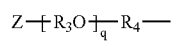

as defined above in which Z is a hydroxy or alkoxy group having 1, 2, 3, 4, 5, or 6 carbon atoms; R$_8$ and R$_{12}$ are each independently alkyl groups having 1, 2, 3, 4, 5, or 6 carbon atoms, straight-chain or branched; R$_9$, R$_{13}$, and R$_{21}$ are each independently selected from a straight-chain or branched alkyl bridging linkage having 1, 2, 3, 4, 5, or 6 carbon atoms; R$_{16}$, R$_{17}$, R$_{18}$, R$_{19}$, R$_{20}$ are each independently selected from hydrogen or an alkyl group having 1, 2, 3, 4, 5, or 6 carbon atoms; d is 0 or 1; and a is any integer between 0 and 100, with the proviso that when X is a moiety of the formula given in iii) above, the sum of a+b+c is any number between 2 and 400. Examples of products falling within this class include those sold by HUNTSMAN LLC of Houston Tex. under the JEFFAMINE® trademark line, including JEFFAMINE® D-230, JEFFAMINE® D-2000, JEFFAMINE® D-400, JEFFAMINE® T-403 and JEFFAMINE® ED series.

More generally, then, according to the invention secondary amines are produced by alkylating corresponding primary amines using ketones or aldehydes in the presence of hydrogen and the catalyst specified herein. Surprisingly, the high conversions observed when carrying out a process according to the invention were obtained with relatively low carbonyl compound to amine ratio, and an insignificant amount of corresponding tertiary amines were obtained in the final product, with no detectable amine coupling product being observed present in the reaction product.

The carbonyl compound used in a process according to the present invention may be thought of as an alkylating agent, which may be either an aldehyde or ketone represented by the structure:

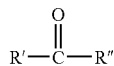

in which R' and R" are each independently selected from the group consisting of: hydrogen; $C_1$–$C_{10}$ alkyl, whether straight-chain, branched or cyclic; or alkylaryl, in which the alkyl portion is straight-chain, branched, or cyclic, subject to the proviso that both R' and R" cannot simultaneously be hydrogen.

While a process according to the present invention may be carried out in either a batch process or continuous process fashion, it is most preferred that the process be carried out in a continuous fashion. According to one preferred form of the invention, the reaction is carried out in a tubular reactor. In practice of such embodiment, the reactor comprises a tube which is charged with particles of the catalyst material, and in which said tube is surrounded by a heat transfer medium, such as a fluid sold under the DOWTHERM® trademark by the Dow Chemical Company, to control the temperature of the reactor. Typically, the tubular reactor is oriented in the vertical direction and the reactants of alkylating agent, hydrogen, and amine are fed into the bottom of the tube, and the product stream emerges from the top portion of the tube and is collected. If desired or necessary, the effluent of the tubular reactor is further processed (e.g., distilled) to yield a purified product.

One unexpected benefit of the present invention owing presumably to the high selectivity and conversion discovered, is that for most practical end uses, the reactor effluent of a process carried out in accordance with the invention requires no further purification steps. This alleviation of further purification leads to a less resource-intensive overall process for producing a particular alkylated amine product, the cost savings of which may be readily passed on to consumers of the products generated, including polyurethane and polyurea products, since the amine products of a process according to the present invention will in may cases be used as catalysts in producing polyurethanes and polyureas.

While the present invention has been constructively reduced by virtue of the foregoing, the inventors now provide accounts in the form of the following written examples, for the convenience of the reader in furtherance of appreciating the scope of the present invention. As such, these examples are thus presented to be exemplary of the inventive process, and not delimitive in any way of the aforesaid disclosure:

EXAMPLE 1

Preparation of N-isopropyl-N',N'-dimethyl-1,3-propylenediamine

Into a jacketed stainless steel tubular upflow reactor (volume=600 cc) having inside diameter of 1.338" and containing a thermowell fabricated from 0.25 O.D. tubing extended upward into the reactor were simultaneously fed 580 g per hour of dimethylaminopropylamine ("DMAPA") and 420 g per hour of acetone were simultaneously fed (upflow). The reactor tube was full of a packed-bed of nickel catalyst such as that disclosed in U.S. Pat. Nos. 3,151,112 and 3,654,370. Hydrogen was fed at about 100% in excess of the stoichiometric amount. The reaction was conducted under a pressure of 1500 psig and at a temperature of 135° C. After a single pass through the approximate 30" length of the tubular reactor, the reactor effluent was analyzed and showed about 85% N-isopropyl-N',N'-dimethyl-1,3-propylenediamine, 6% unreacted DMAPA; 1% di-isopropyl DMAPA; and 2% coupling product. Also, di-isopropyl DMAPA failed to separate from DMAPA during the subsequent distillation of the product.

EXAMPLE 2

Preparation of N-isoropyl-N',N'-dimethyl-1,3-propylenediamine

The procedure of Example 1 was repeated, with the exception that the nickel catalyst used previously was replaced by a 1% palladium on carbon catalyst (Engelhard) and the reaction temperature was reduced to 120° C. The effluent was analyzed and gave about 97% yield of N-isopropyl-N',N'-dimethyl-1,3-propylenediamine. No significant amounts of di-isopropyl DMAPA or coupling products were detected. The effluent was distilled to give 99.5% pure N-isopropyl-N',N'-dimethyl-1,3-propylenediamine.

EXAMPLE 3

Preparation of N,N'-Diisopropylisophorone Diamine

About 300 g per hour of isophorone diamine and 450 g per hour of acetone were fed upflow into a 600 cc packed-bed reactor filled with a nickel catalyst as described in example 1 above. Hydrogen was fed at about 100% in excess. The reaction was conducted at 2000 psig and 140° C. Lights were stripped out of the reactor effluent under reduce pressure. The resulting product was analyzed to contain 8.78 meq/g of total amine and 3.557 meq/g of primary amine. This result indicates that a significant amount (40.5%) of primary amine group was not alkylated. Also, GC analysis showed about 2.00% of "heavies" were present. In other words, amine coupling had occurred.

EXAMPLE 4

Preparation of N,N'-Diisopropylisophorone Diamine

A 200 cc DOWTHERM® heated stainless steel tubular upflow reactor which has an inside diameter of 0.815" and a thermostat fabricated from 0.25" OD tubing extend upwardly into the reactor was used. The reactor was filled with a 1.0% palladium on carbon catalyst (Engelhard). About 100 g per hour of isophorone diamine and 135 g per hour of acetone was fed into the tubular reactor, simultaneously, along with hydrogen at about 100% in excess. The reaction was conducted at 2000 psig and 150° C. Lights were stripped out of the reactor effluent under reduce pressure. The resulting product was analyzed to contain 7.89 meq/g of total amine, 0.07 meq/g of primary amine, and 0.04 meq/g of tertiary amine. GC analysis also showed no evidence of coupling. This result indicates, with Pd/C catalyst, high conversion and selectivity were achieved.

EXAMPLE 5

COMPARATIVE EXAMPLE

The procedure of example 4 was followed. However, equal mass amounts of isophorone diamine and acetone were fed, and space velocity was 1.3 g/hr total liquid feed per cc catalyst. The resulting product was analyzed to contain 7.83 meq/g of total amine, and 0.16 meq/g of tertiary amine. No primary amine was detected. In other words, the product consisted of greater than 99 wt. % secondary amine and less than 0.2 wt. % tertiary amine. Again, the result demonstrated that, with Pd/C catalyst, high conversion and high selectivity can be obtained even at lower ketone to amine ratio.

EXAMPLE 6

Preparation of N,N'-Diisopropyl JEFFAMINE® D-230

The procedure of example 4 is followed except that JEFFAMINE® D-230 and acetone were fed at about 150 g per hour, each. The reaction was conducted at 180° C. The resulting product was analyzed to contain 6.15 meq/g of total amine, 0.03 meq/g of tertiary amine, and 0.09 meq/g of primary amine.

EXAMPLE 7

Preparation of N,N'-Diisopropyl JEFFAMINE® D-2000

The procedure of example 4 was followed except that JEFFAMINE® D-2000 and acetone were fed at 200 g per hour and 80 g per hour, respectively. The reaction was conducted at 200° C. The resulting product was analyzed to contain 0.96 meq/g of total amine, 0.01 meq/g of tertiary amine, and 0.02 meq/g of primary amine.

EXAMPLE 8

Preparation of N,N',N"-Triisopropyl JEFFAMINE® T-403

The procedure of example 4 was followed except that JEFFAMINE® T-403 and acetone were fed at 150 g per hour and 130 g per hour, respectively. The reaction was conducted at 190° C. The resulting product was analyzed to contain 5.11 meq/g of total amine, 0.07 meq/g of tertiary amine, and 0.10 meq/g of primary amine.

The present invention may be carried out using such reactants as all known primary amines, and including dimethylaminopropylamine, monoethanolamine, DGA® agent (available from Huntsman LLC of Houston, Tex.) and JEFFAMINE® amine products, also available from Huntsman LLC as raw materials.

We have discovered that by using a catalyst of palladium on carbon, that high conversion and selectivity to secondary amine is obtained when reacting isophorone diamine with acetone in the presence of hydrogen. Palladium has been known previously as a reductive amination catalyst; however, in the known cases this catalyst was only found useful for making tertiary amines using ketones, as the alkylation according to prior art methods would not cease at the secondary amine stage, but would proceed uncontrollably to a tertiary amine product. Thus, the present invention relates to a process to selectively produce secondary amines, in high yield, by reacting a primary amine with a ketone in the presence of hydrogen using a catalyst comprising palladium on carbon.

Consideration must be given to the fact that although this invention has been shown and described with respect to certain preferred embodiments, it is obvious that equivalent alterations and modifications will occur to others skilled in the art upon the reading and understanding of this specification and the claims appended hereto. The present invention includes all such equivalent alterations and modifications, and is limited only by the scope of the claims which follow.

What is claimed is:

1. A process for producing a secondary amine product which comprises heating a mixture comprising: a) hydrogen; b) a carbonyl compound represented by:

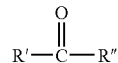

and c) a primary amine reactant represented by the structure R—NH$_2$ to any temperature in the range of about 80° C. to about 230° C. and under any pressure in the range of about 100 psig to about 3000 psig in the presence of an effective catalytic amount of a catalyst comprising metallic palladium, wherein said secondary amine product has the formula:

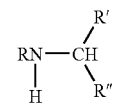

in which R is any alkyl, aminoalkyl, alkylaryl, or aminoalkylaryl group, whether straight-chain, branched, or cyclic, R' and R" are each independently selected from the group consisting of:

hydrogen; $C_1$–$C_{20}$ alkyl, whether straight-chain, branched, or cyclic, subject to the proviso that both R' and R" are not simultaneously hydrogen, wherein the amount of tertiary amine produced during said process is less than 3.00% by weight of the total amount of secondary amine produced, and further wherein the secondary amine product is produced in a yield of at least 97.00% by weight based on all amine products produced.

2. A process according to claim 1 in which said catalyst has a surface area of at least 100 m² per gram.

3. A process according to claim 1 in which said primary amine reactant is a diamine.

4. A process according to claim 3 wherein said diamine contains two —NH₂ groups.

5. A process according to claim 1 in which the amount of tertiary amine impurity produced is less than 2.0% by weight based on all amine products produced.

6. A process according to claim 1 wherein said catalyst comprises palladium on carbon.

7. A process according to claim 6 wherein said carbon comprises charcoal.

8. A process according to claim 1 wherein said carbonyl compound comprises a ketone selected from the group consisting of: acetone, methylethyl ketone, methylisobutyl ketone, methylisoamyl ketone, 2-butanone, 2-pentanone, 2-hexanone, and 2-ethylhexanone.

9. A process according to claim 3 in which said primary amine is isophorone diamine, said carbonyl compound is acetone, and in which the product N,N'-Diisopropylisophorone Diamine is produced in a yield of at least 97.00% by weight based on all amine products produced.

10. A process according to claim 3 in which said primary amine is isophorone diamine, said carbonyl compound is acetone, and in which amount of tertiary amine impurity produced is less than 2.0% by weight based on all amine products produced.

11. A process for producing a secondary amine product from a primary amine reactant, which process comprises heating a mixture that comprises the components:
a) hydrogen;
b) a carbonyl compound represented by the structure:

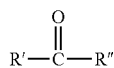

in which R' and R" are each independently selected from the group consisting of: hydrogen; $C_1$–$C_{20}$ alkyl, whether straight-chain, branched, or cyclic, subject to the proviso that both R' and R" are not simultaneously hydrogen, and
c) an amine reactant comprising one or more alkoxylated amines having a primary amine function and described by the formula:

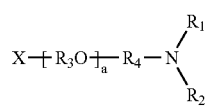

in which $R_1$ and $R_2$ are each independently selected from the group consisting of: hydrogen; an alkyl group having 1, 2, 3, 4, 5, or 6 carbon atoms, whether straight-chain or branched; or a radical of the formula:

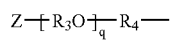

in which $R_3$ may be an alkyl group having any number of carbon atoms selected from 1, 2, 3, 4, 5, or 6, straight-chain or branched; $R_4$ is a straight-chain or branched alkyl bridging group having 1, 2, 3, 4, 5, or 6 carbon atoms; Z is a hydroxy group or alkyl group containing 1, 2, 3, 4, 5, or 6 carbon atoms, straight-chain or branched; q is any integer between 0 and 400; and wherein X is any of:

i) a hydroxy group or an alkyl group having any number of carbon atoms selected from 1, 2, 3, 4, 5, or 6; or

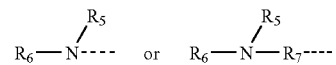

ii) a group in which $R_5$ and $R_6$ are each independently selected from the group consisting of: hydrogen; an alkyl group having 1, 2, 3, 4, 5, or 6 carbon atoms, whether straight-chain or branched; or

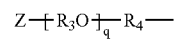

as defined above in which Z is a hydroxy group or an alkoxy group having 1, 2, 3, 4, 5, or 6 carbon atoms, and in which $R_7$ is a straight-chain or branched alkylene bridging group having 1, 2, 3, 4, 5, or 6 carbon atoms; or iii) a moiety of the formula:

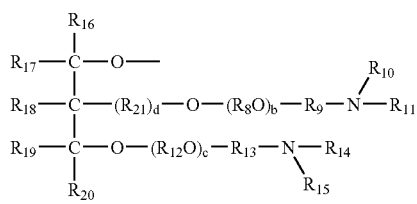

in which $R_{10}$, $R_{11}$, $R_{14}$, and $R_{15}$ are each independently selected from the group of: hydrogen; an alkyl group having 1, 2, 3, 4, 5, or 6 carbon atoms, straight-chain or branched; the moiety

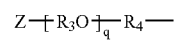

as defined above in which Z is a hydroxy or alkoxy group having 1, 2, 3, 4, 5, or 6 carbon atoms; $R_8$ and $R_{12}$ are each independently alkyl groups having 1, 2, 3, 4, 5, or 6 carbon atoms, straight-chain or branched; $R_9$, $R_{13}$, and $R_{21}$ are each independently selected from a straight-chain or branched alkyl bridging linkage having 1, 2, 3, 4, 5, or 6 carbon atoms; $R_{16}$, $R_{17}$, $R_{18}$, $R_{19}$, $R_{20}$ are each independently selected from hydrogen or an alkyl group having 1, 2, 3, 4, 5, or 6 carbon atoms; d is 0 or 1; and a is any integer between 0 and 100, with the proviso that when X is a moiety of the formula given in iii) above, the sum of a+b+c is any number between 2 and 400, to any temperature in the range of about 80° C. to about 200° C. and under any pressure in the range of about 100 psig to about 3000 psig in the presence of an effective catalytic amount of a catalyst comprising metallic palladium, wherein the total amount of tertiary amine produced during said process is less than 3.00% by weight of the total amount of secondary amine produced, and further wherein the secondary amine product is produced in a yield of at least 97.00% by weight based on all amine products produced.

12. A process according to claim 11 in which said catalyst has a surface area of at least 100 m² per gram.

13. A process according to claim 11 in which said amine reactant is a diamine.

14. A process according to claim 13 wherein said diamine contains two —NH$_2$ groups.

15. A process according to claim 11 in which the amount of tertiary amine impurity produced is less than 2.0% by weight based on all amine products produced.

16. A process according to claim 11 wherein said catalyst comprises palladium on carbon.

17. A process according to claim 16 wherein said carbon comprises charcoal.

18. A process according to claim 11 wherein said carbonyl compound comprises a ketone selected from the group consisting of: acetone, methylethyl ketone, methylisobutyl ketone, methylisoamyl ketone, 2-butanone, 2-pentanone, 2-hexanone, and 2-ethyihexanone.

* * * * *